(12) United States Patent
Hutchens

(10) Patent No.: US 9,480,505 B2
(45) Date of Patent: Nov. 1, 2016

(54) BI-PLANAR PERSUADER

(75) Inventor: Christopher Hutchens, Granite Bay, CA (US)

(73) Assignee: DePuy Synthes Products, Inc., Raynham, MA (US)

( * ) Notice: Subject to any disclaimer, the term of this patent is extended or adjusted under 35 U.S.C. 154(b) by 653 days.

(21) Appl. No.: 13/592,526

(22) Filed: Aug. 23, 2012

(65) Prior Publication Data
US 2014/0058464 A1 Feb. 27, 2014

(51) Int. Cl.
*A61B 17/70* (2006.01)

(52) U.S. Cl.
CPC ....... *A61B 17/7086* (2013.01); *A61B 17/7085* (2013.01)

(58) Field of Classification Search
USPC .......................................... 606/104, 86 A, 99
See application file for complete search history.

(56) References Cited

U.S. PATENT DOCUMENTS

| | | | | |
|---|---|---|---|---|
| 4,271,836 A * | 6/1981 | Bacal | .................. | A61B 17/025 29/268 |
| 4,411,259 A | 10/1983 | Drummond | | |
| 5,020,519 A * | 6/1991 | Hayes | .................. | A61B 17/025 600/226 |
| 5,616,143 A * | 4/1997 | Schlapfer | ........... | A61B 17/7032 606/205 |
| 5,720,751 A * | 2/1998 | Jackson | ............. | A61B 17/7032 606/104 |
| 5,863,293 A * | 1/1999 | Richelsoph | ........ | A61B 17/7037 606/271 |
| 5,910,141 A * | 6/1999 | Morrison | ........... | A61B 17/7091 606/101 |
| 6,015,413 A * | 1/2000 | Faccioli | ............. | A61B 17/8891 606/104 |
| 6,123,707 A * | 9/2000 | Wagner | .............. | A61B 17/7037 606/279 |
| 6,551,316 B1 | 4/2003 | Rinner et al. | | |
| 6,648,888 B1 | 11/2003 | Shluzas | | |
| 6,726,692 B2 * | 4/2004 | Bette | ................... | A61B 17/7088 606/264 |
| 6,746,449 B2 * | 6/2004 | Jones | ................. | A61B 17/7037 606/279 |
| 6,790,208 B2 * | 9/2004 | Oribe | ................. | A61B 17/7083 606/104 |
| 7,004,947 B2 | 2/2006 | Shluzas et al. | | |
| 7,090,679 B2 * | 8/2006 | Saint-Martin | ...... | A61B 17/7032 606/99 |
| 7,278,995 B2 | 10/2007 | Nichols et al. | | |
| 7,371,239 B2 * | 5/2008 | Dec | .................... | A61B 17/7088 606/103 |
| 7,462,182 B2 * | 12/2008 | Lim | ................... | A61B 17/7086 606/99 |
| 7,572,281 B2 * | 8/2009 | Runco | ................ | A61B 17/7086 606/246 |
| 7,611,517 B2 | 11/2009 | Lim | | |
| 7,618,444 B2 | 11/2009 | Shluzas | | |

(Continued)

FOREIGN PATENT DOCUMENTS

EP 1374786 A2 1/2004

*Primary Examiner* — Lynnsy Summitt
(74) *Attorney, Agent, or Firm* — Meunier Carlin & Curfman LLC

(57) ABSTRACT

Surgical instruments for spinal surgery. More specifically, a bi-planar rod persuader for urging a spinal rod into a screw, and methods regarding the same. The bi-planar rod persuader may include an implant holder, which may also include a holding sleeve. A securing foot may be attached to the distal end of the holding sleeve, and the holding sleeve may also include a threaded opening at the proximal end for receiving a stem that drives the securing foot between a first position and second position. The implant holder may also include a threaded part to engage a reduction knob. A handle assembly may also be provided, which may include two pivotally attached arms. A rod hook may be connected to one of the arms and a guide attached to the other of the arms.

17 Claims, 11 Drawing Sheets

(56) References Cited

U.S. PATENT DOCUMENTS

| | | | | |
|---|---|---|---|---|
| 7,625,376 B2* | 12/2009 | Brumfield | ............... | B25B 7/18 606/86 A |
| 7,686,814 B2 | 3/2010 | Lim et al. | | |
| 7,722,617 B2* | 5/2010 | Young | ............... | A61B 17/7086 606/86 A |
| 7,744,598 B2 | 6/2010 | Brumfield et al. | | |
| 7,758,584 B2* | 7/2010 | Bankoski | ........... | A61B 17/7076 606/104 |
| 7,776,074 B2* | 8/2010 | Bray | ................. | A61B 17/7041 606/279 |
| 7,799,031 B2* | 9/2010 | Miller | ................ | A61B 17/7088 606/279 |
| 7,811,288 B2 | 10/2010 | Jones et al. | | |
| 7,824,411 B2* | 11/2010 | Varieur | .............. | A61B 17/7086 606/86 A |
| 7,842,044 B2* | 11/2010 | Runco | ................ | A61B 17/7076 606/104 |
| 7,887,541 B2* | 2/2011 | Runco | ................ | A61B 17/7086 606/279 |
| 7,922,749 B2* | 4/2011 | Dewey | ............... | A61B 17/7086 606/246 |
| 7,927,334 B2* | 4/2011 | Miller | ................ | A61B 17/7088 606/86 A |
| 7,988,698 B2* | 8/2011 | Rosenberg | ......... | A61B 17/7086 606/265 |
| 8,105,329 B2* | 1/2012 | Brumfield | .......... | A61B 17/7088 606/279 |
| 8,128,629 B2* | 3/2012 | Barry | ................ | A61B 17/7086 606/205 |
| 8,137,357 B2* | 3/2012 | Barry | ................ | A61B 17/7074 606/205 |
| RE43,526 E * | 7/2012 | Morrison | ........... | A61B 17/7091 606/86 A |
| 8,211,111 B2* | 7/2012 | Dauster | .............. | A61B 17/7086 606/86 A |
| 8,216,241 B2* | 7/2012 | Runco | ................ | A61B 17/7032 606/104 |
| 8,221,474 B2* | 7/2012 | Bridwell | ............... | A61B 17/025 606/279 |
| 8,246,623 B2* | 8/2012 | Peultier | .............. | A61B 17/7086 606/246 |
| 8,246,625 B2* | 8/2012 | Miller | ................ | A61B 17/7088 606/279 |
| 8,308,729 B2* | 11/2012 | Nunley | .............. | A61B 17/7086 606/79 |
| 8,449,549 B2* | 5/2013 | Barry | ................ | A61B 17/7074 606/205 |
| RE44,296 E * | 6/2013 | Beale | ................ | A61B 17/7086 606/104 |
| 8,460,300 B2* | 6/2013 | Hestad | ............... | A61B 17/7085 606/86 A |
| 8,491,588 B2* | 7/2013 | Wall | .................... | A61B 17/7079 606/104 |
| 8,556,903 B2* | 10/2013 | Miller | ................ | A61B 17/7088 606/86 A |
| 8,617,165 B2* | 12/2013 | Harper | .............. | A61B 17/7083 606/86 A |
| 8,636,742 B2* | 1/2014 | Runco | ................ | A61B 17/7086 606/86 A |
| 8,636,776 B2* | 1/2014 | Rosenberg | ......... | A61B 17/7086 606/270 |
| 8,647,347 B2* | 2/2014 | Runco | ................ | A61B 17/7032 606/86 A |
| RE44,813 E * | 3/2014 | Beale | ................ | A61B 17/7086 606/104 |
| 2003/0028195 A1* | 2/2003 | Bette | ................ | A61B 17/7088 606/86 R |
| 2004/0249378 A1* | 12/2004 | Saint Martin | ...... | A61B 17/7032 606/86 A |
| 2004/0267275 A1* | 12/2004 | Cournoyer | ......... | A61B 17/7086 606/99 |
| 2005/0059969 A1* | 3/2005 | McKinley | .......... | A61B 17/7086 606/86 A |
| 2006/0009775 A1* | 1/2006 | Dec | .................... | A61B 17/7088 606/86 R |
| 2006/0025768 A1* | 2/2006 | Iott | .................... | A61B 17/7032 606/86 A |
| 2006/0111730 A1* | 5/2006 | Hay | ................... | A61B 17/7088 606/104 |
| 2006/0293692 A1* | 12/2006 | Whipple | ............ | A61B 17/7032 606/104 |
| 2007/0161998 A1* | 7/2007 | Whipple | ............ | A61B 17/7086 606/86 A |
| 2007/0162009 A1* | 7/2007 | Chao | .................. | A61B 17/8866 606/86 A |
| 2007/0260261 A1* | 11/2007 | Runco | ................ | A61B 17/7032 606/104 |
| 2007/0270867 A1* | 11/2007 | Miller | ................ | A61B 17/7088 606/86 R |
| 2007/0270868 A1* | 11/2007 | Dewey | ............... | A61B 17/7086 606/86 R |
| 2007/0270869 A1* | 11/2007 | Young | ................ | A61B 17/7086 606/86 R |
| 2008/0004629 A1 | 1/2008 | Nichols et al. | | |
| 2008/0154277 A1* | 6/2008 | Machalk | ............ | A61B 17/7091 606/99 |
| 2008/0195155 A1* | 8/2008 | Hoffman | ............ | A61B 17/7091 606/278 |
| 2008/0221626 A1 | 9/2008 | Butters et al. | | |
| 2008/0228233 A1* | 9/2008 | Hoffman | ............ | A61B 17/7088 606/86 A |
| 2009/0018593 A1* | 1/2009 | Barrus | ............... | A61B 17/7086 606/86 A |
| 2009/0228054 A1 | 9/2009 | Hoffman et al. | | |
| 2009/0228055 A1 | 9/2009 | Jackson | | |
| 2009/0259262 A1 | 10/2009 | Nayet | | |
| 2009/0281582 A1 | 11/2009 | Villa et al. | | |
| 2010/0004695 A1 | 1/2010 | Stad et al. | | |
| 2010/0030283 A1 | 2/2010 | King et al. | | |
| 2010/0069972 A1 | 3/2010 | Jones et al. | | |
| 2010/0121385 A1 | 5/2010 | Blain et al. | | |
| 2010/0121386 A1 | 5/2010 | Peultier et al. | | |
| 2010/0185242 A1 | 7/2010 | Barry et al. | | |
| 2010/0185248 A1 | 7/2010 | Barry et al. | | |
| 2010/0228302 A1 | 9/2010 | Dauster et al. | | |
| 2010/0280560 A1 | 11/2010 | Brumfield et al. | | |
| 2011/0054549 A1 | 3/2011 | Miller et al. | | |
| 2011/0093022 A1* | 4/2011 | Runco | ................ | A61B 17/7076 606/86 A |
| 2011/0118791 A1* | 5/2011 | Nunley | .............. | A61B 17/7086 606/279 |
| 2011/0172723 A1 | 7/2011 | Miller et al. | | |
| 2011/0245884 A9 | 10/2011 | Brumfield et al. | | |
| 2013/0018419 A1* | 1/2013 | Rezach | .............. | A61B 17/7076 606/264 |
| 2013/0046344 A1* | 2/2013 | Nunley | .............. | A61B 17/7086 606/258 |
| 2013/0261636 A1* | 10/2013 | Barry | ................ | A61B 17/7074 606/104 |
| 2013/0317558 A1* | 11/2013 | Varieur | .............. | A61B 17/7076 606/86 A |

* cited by examiner

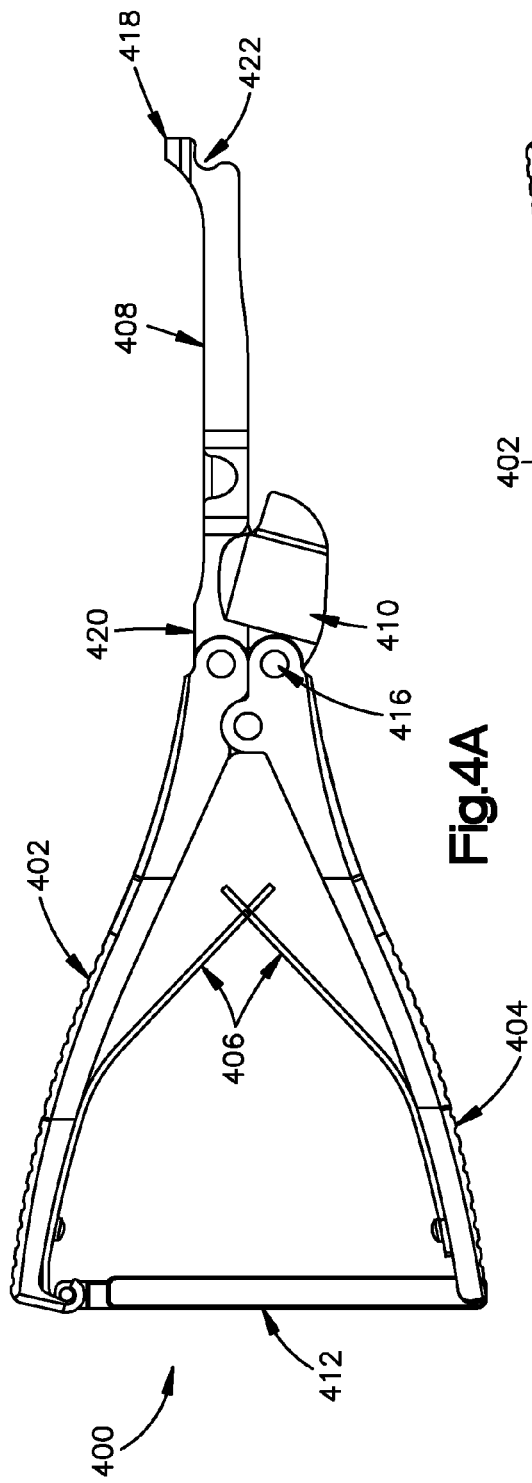
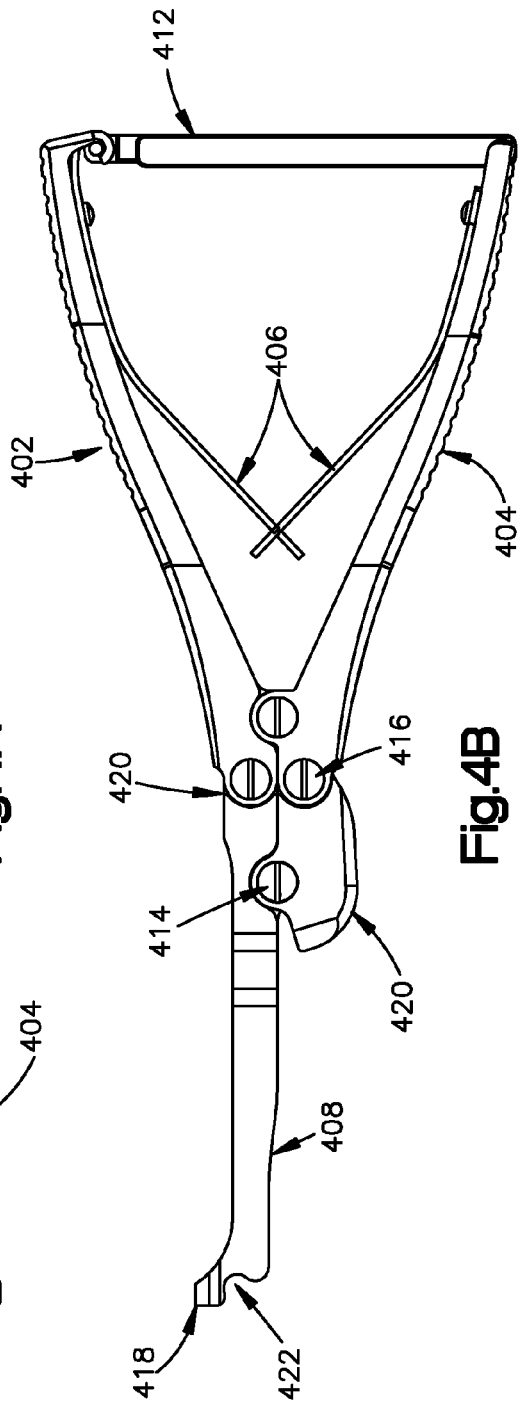
Fig.4A
Fig.4B

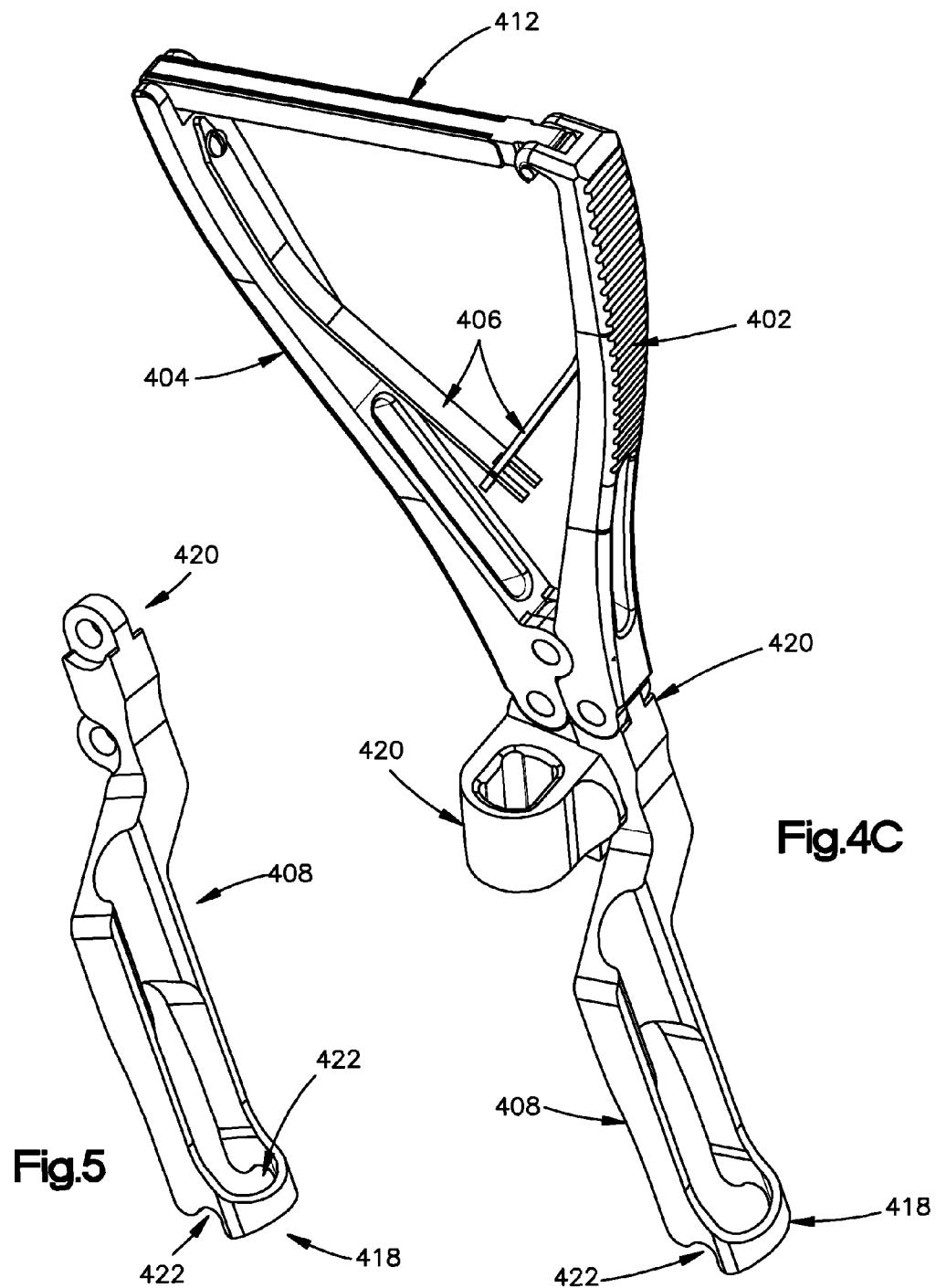

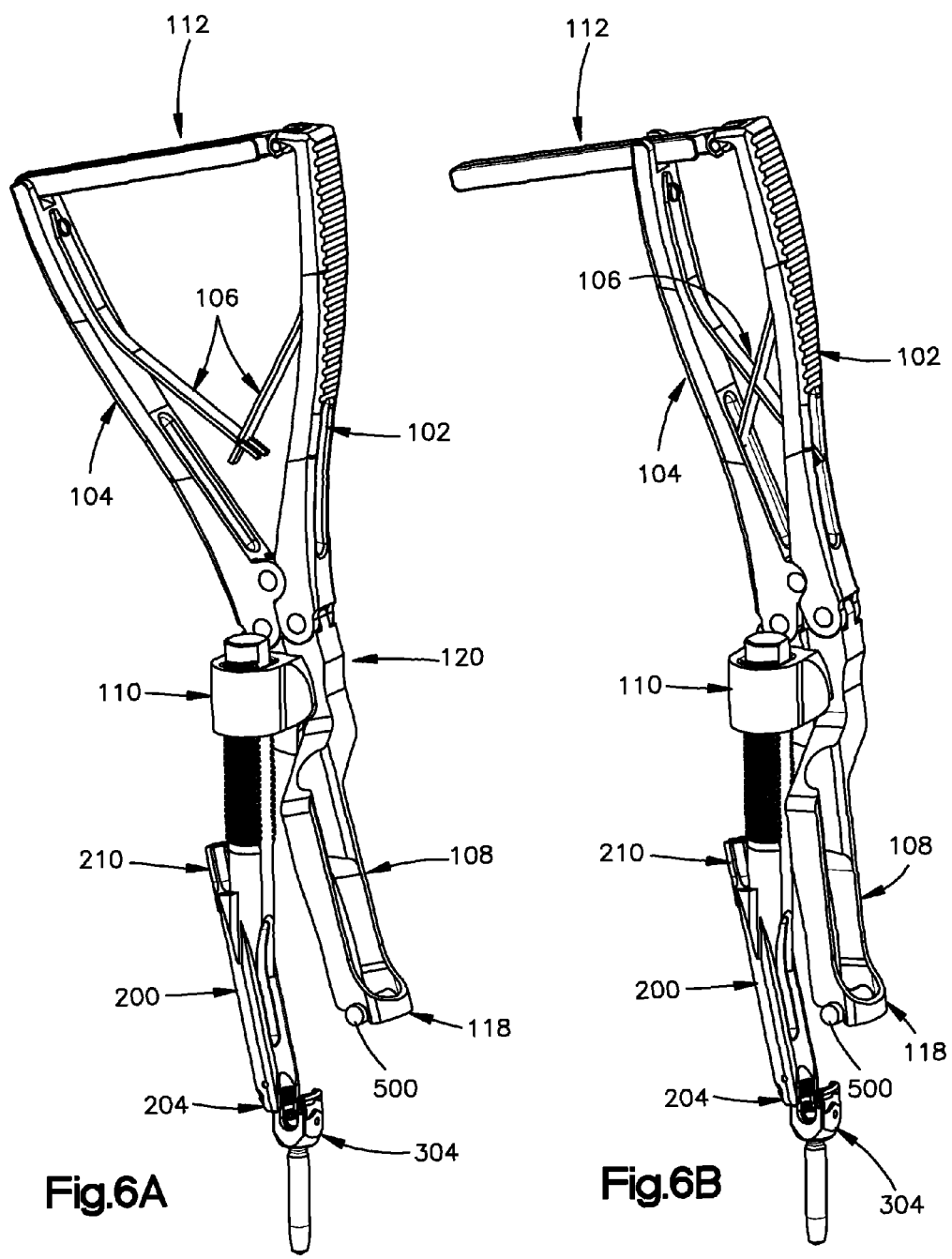

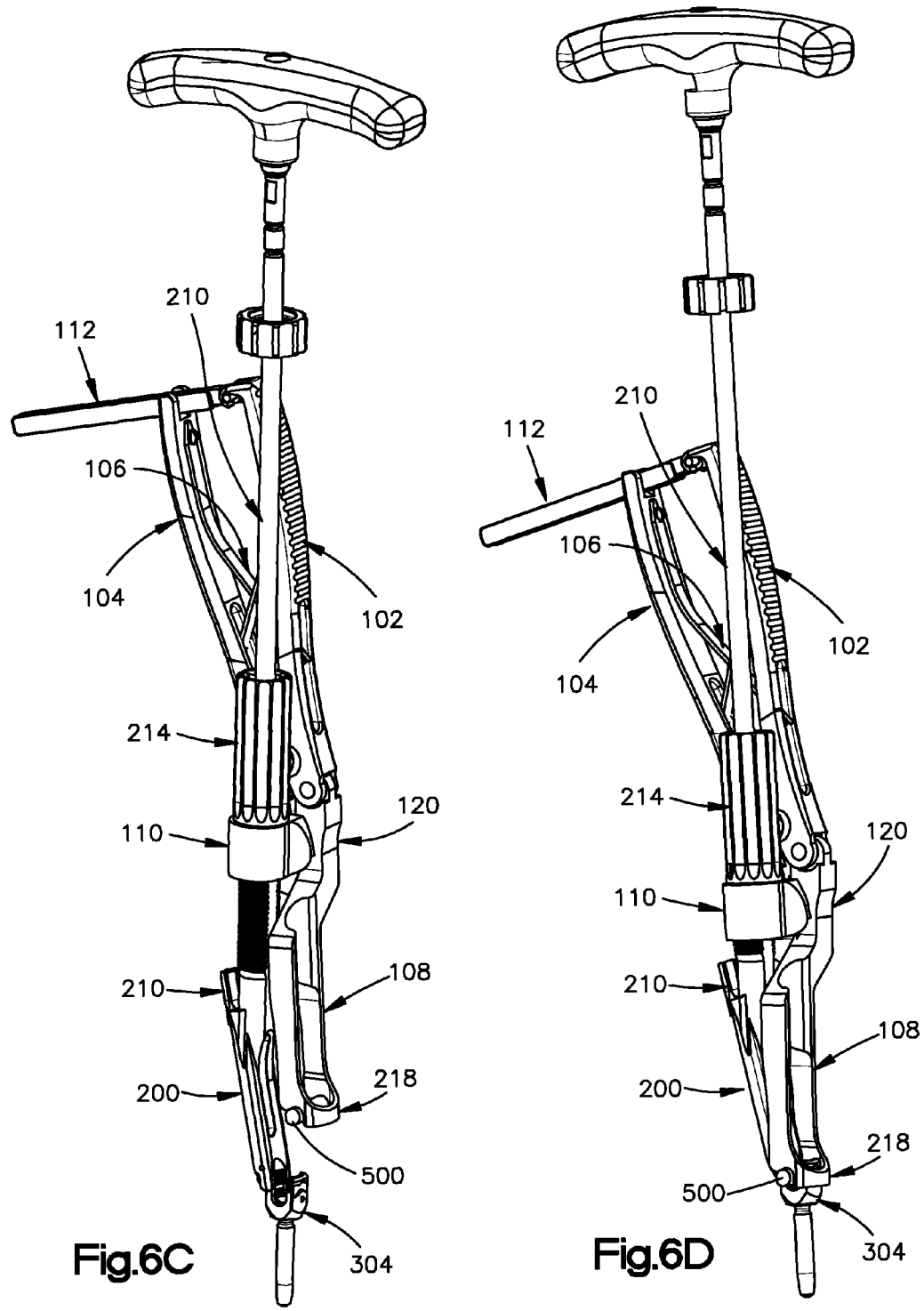

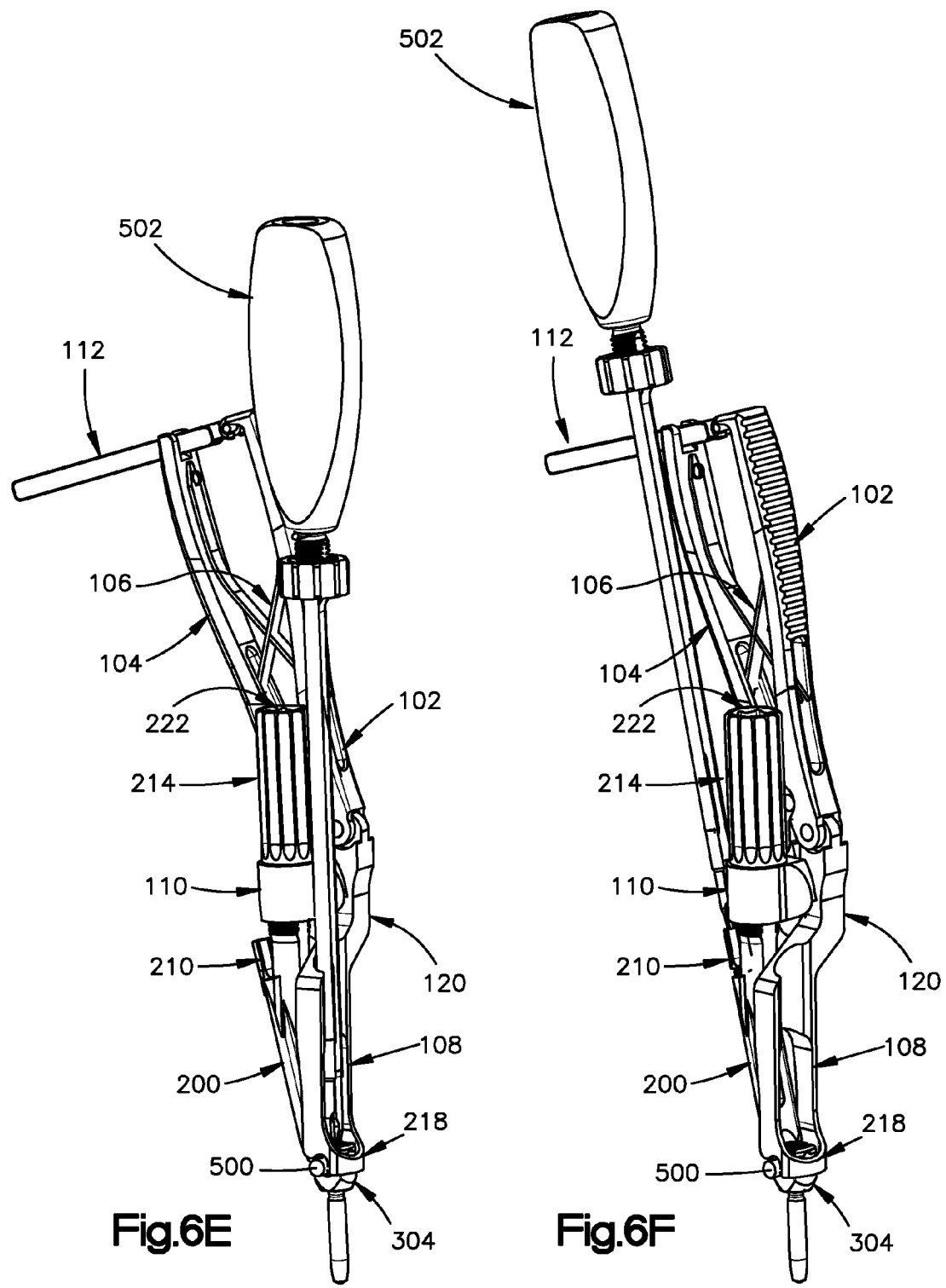

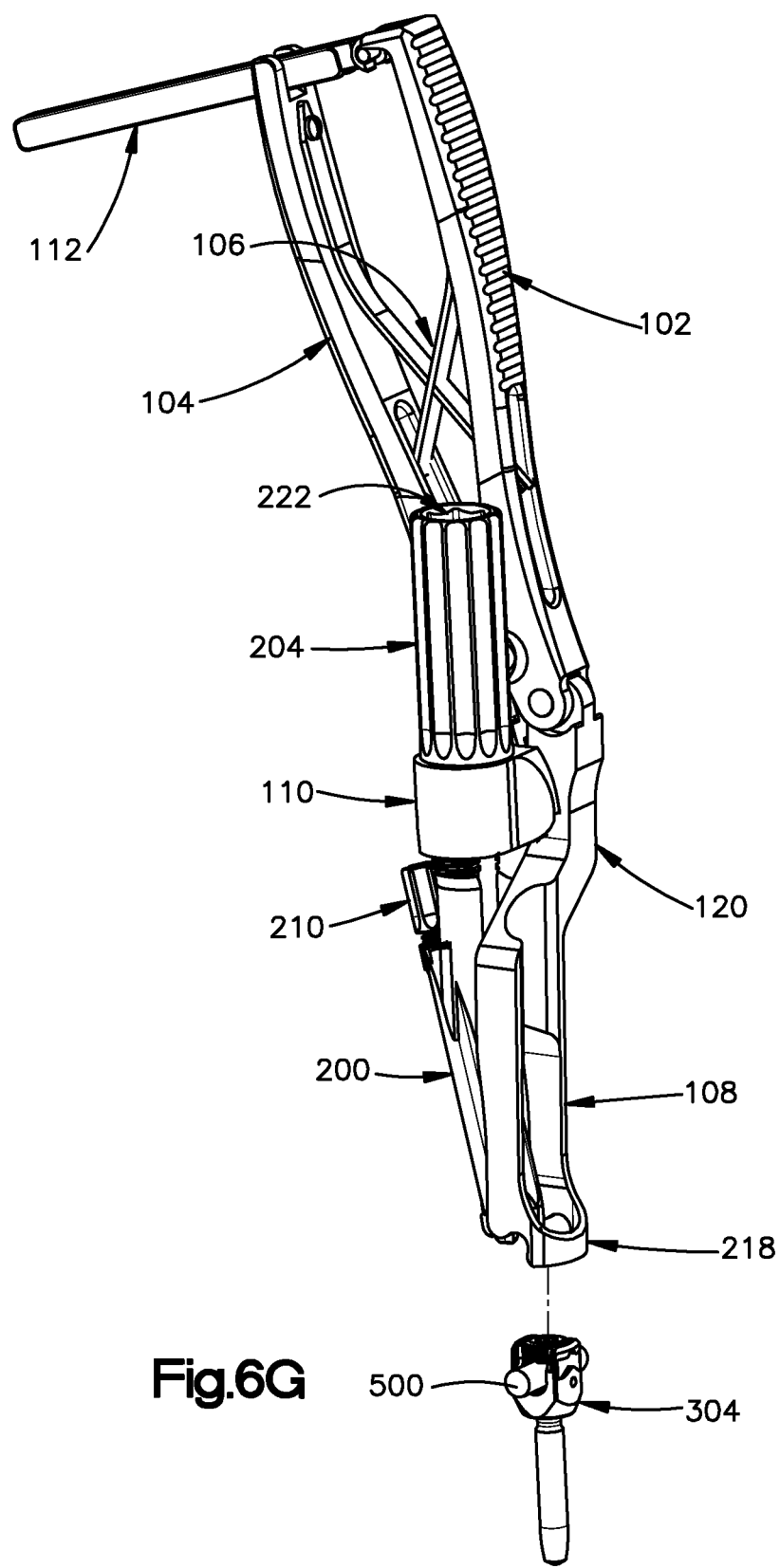

BI-PLANAR PERSUADER

BACKGROUND

The spinal column is a highly complex system of bones and connective tissues that provides support for the body and protects the delicate spinal cord and nerves. The spinal column includes a series of vertebral bodies stacked together. An intervertebral disc is positioned between each vertebral body, and these intervertebral discs cushion and dampen compressive forces exerted upon the spinal column.

However, when there is a spinal disorder, procedures are performed to surgically correct and stabilize spinal curvatures or to facilitate spinal fusion. Spinal column disorders include scoliosis, kyphosis, excess lordosis, spondylolisthesis, and other disorders caused by abnormalities, disease or trauma, such as ruptured or slipped discs, degenerative disc disease, fractured vertebra, and the like. Patients that suffer from such conditions usually experience extreme and debilitating pain, as well as diminished nerve function.

Spinal fixation is one surgical technique that may be used to effectively treat the above-described conditions and, in many cases, to relieve pain. Spinal fixation involves the use of spinal implants and/or mechanical immobilization to fuse two or more vertebral bodies of the spinal column. Furthermore, spinal fixation may be used to alter the alignment of adjacent vertebral bodies relative to one another so as to change the overall alignment of the spinal column.

One such spinal fixation technique involves immobilizing the spine using orthopedic stabilizing rods, commonly referred to as spinal rods, which are positioned generally parallel to the spine. Each rod is attached to various vertebra along the length of the spine by way of vertebra engaging spinal implants which may include, but are not limited to, pedicle screws, pedicle hooks, transverse process hooks, sublaminar hooks, etc. The spinal implants commonly include a U-shaped rod receiving channel for receiving the spinal rod therein. Moreover, the rod receiving channel often includes a means for receiving a fastening mechanism, for example, a set screw, a locking screw, or a cam, to subsequently clamp and fix the position of the spinal rod with respect to the spinal implant.

Instruments are commonly used to insert the spinal rod into position in the receiving channel. Surgeons, however, have often encountered considerable difficulty when using these instruments because of problems associated with aligning the spinal rod(s) within the rod receiving channel(s) formed in the head(s) of the spinal implant(s). For example, the heads of the spinal implants may be out of vertical and/or horizontal alignment with one another due to the curvature of the spine or the size and shape of each vertebrae.

SUMMARY

The present disclosure relates to a medical device for reducing a spinal rod into the head of a screw, and methods for using such device. These devices and methods may be used with surgeries involving spinal fixation.

An example medical device for reducing a spinal rod into the head of a pedicle screw includes an implant holder and a handle assembly. The implant holder includes a holding sleeve, which has a proximal end and a distal end. The holding sleeve is configured such that a securing foot is pivotally attached to the distal end. Furthermore, the proximal end of the holding sleeve includes a threaded opening, into which a stem is inserted. For example, the stem has a proximal end and distal end. The stem drives the securing foot between a first position and a second position. The implant holder also includes a threaded part that extends at a predetermined angle from the proximal end of the holding sleeve. This threaded part is adapted to engage a complementary threaded region of a reduction knob. The handle assembly includes two pivotally attached arms. A rod hook is connected to one of the arms, and a guide is attached to the other arm.

The guide is adapted to slidably engage the threaded part. The rod hook is moveable in a first direction by threaded interaction of the reduction knob with the threaded part. The rod hook is moveable in a second direction that is different than the first direction through pivotal motion of the arms.

The distal end of the stem may optionally include a spherical shape and a ridge area, and the proximal end of the stem may include a securing cap. For example, the securing cap may include a recessed portion, which has a known geometric shape for insertion of a tightening instrument, such as a T25 driver. The stem also may include a threaded region for a predetermined distance on the part of the stem proximate to the securing cap. This predetermined distance is optionally less than the length of the stem.

The securing foot is moveable between a first position and a second position. For example, the securing foot is in the first position when the threaded regions of the stem and the holding sleeve are unthreaded. The securing foot is optionally moveable to a second position when the stem is rotated therein the threaded opening of the holding sleeve. The rotation of the stem into the threaded opening of the holding sleeve may engage the securing foot to a screw head. The portion of the securing foot engaging the screw optionally has a known geometry and is complementary to the known geometry of the screw.

The distal end of the holding sleeve optionally includes three sides, and one of the three sides may have a recessed portion. The two of the three unrecessed sides of the holding sleeve may include concave areas for engaging a screw. The distal end of the holding sleeve may also include a ridge portion for engaging a screw.

A guide may optionally be attached to the rod hook with a pivot screw. The distal end of the rod hook may include two concave portions that may be used to engage a spinal rod. Once the rod hook engages a spinal rod, the spinal rod may be moved in a first direction or a second direction. The first direction may be defined as substantially parallel along an axis defining the threaded part. On the other hand, the second direction may be defined by an axis that may be approximated by an arc, and the second direction is substantially perpendicular to the axis defining the first direction. The threaded part of the implant holder may be positioned at a predetermined angle, and that predetermined angle may optionally be approximately 12°.

An adapter rod may also be provided. For example, the adapter rod may have a proximal end and a distal end, and both the proximal end and distal end may have a known geometry. The distal end of the adapter rod may optionally be engaged with the recessed portion of the reduction knob. To advance the reduction knob along the threaded part in a first direction, the adapter rod may be rotated. This advancement of the reduction knob along the threaded part in a first direction optionally causes a spinal rod to engage a pedicle screw. The threaded part of the holding sleeve may include the use of a modified square thread measuring approximately 10°.

The reduction knob may optionally be comprised of polyether ether ketone (PEEK). The threaded portion of the holding sleeve may be comprised of diamond-like carbon coating.

Another example medical device for reducing a spinal rod into the head of a pedicle screw includes an implant holder and a handle assembly. The implant holder includes a holding sleeve, which has a proximal end and a distal end. The holding sleeve is configured such that a securing foot is pivotally attached to the distal end. Furthermore, the proximal end of the holding sleeve includes a threaded opening, into which a stem is inserted. For example, the stem has a proximal end and distal end. The stem drives the securing foot between a first position and a second position. The implant holder also includes a threaded part that extends at a predetermined angle from the proximal end of the holding sleeve. This threaded part is adapted to engage a complementary threaded region of a reduction knob. The handle assembly includes two pivotally attached arms. A rod hook is connected to one of the arms, and a guide is attached to the other arm.

The guide is adapted to slidably engage the threaded part. The rod hook is moveable in a first direction by threaded interaction of the reduction knob with the threaded part. The first direction is defined as substantially parallel along an axis defining the threaded part. The rod hook is also moveable in a second direction that is different than the first direction through pivotal motion of the arms. The second direction is defined as substantially parallel to an axis that may be approximated by an arc created by the movement of the rod hook. The second direction is substantially perpendicular to the axis defining the first direction.

Also provided is a method for reducing a spinal rod into the head of a screw. The method includes attaching a rod hook to a spinal rod. A securing foot is then advanced from a first position to a second position, in order to attach the securing foot and holding sleeve to a screw. The method also includes moving the rod hook in the first direction, and then moving the rod hook in the second direction that is different than the first direction. The movement in the first direction and second direction may be iterative to achieve a final position of the rod.

A locking cap may be optionally introduced to secure the spinal rod to the screw. The method may also include advancing the securing foot from the second position to the first position to detach the securing foot and holding sleeve from the screw.

These and other features and advantages of the implementations of the present disclosure will become more readily apparent to those skilled in the art upon consideration of the following detailed description and accompanying drawings, which describe both the preferred and alternative implementations of the present disclosure.

BRIEF DESCRIPTION OF THE DRAWINGS

In the drawings, like reference numbers and designations in the various drawings indicate like elements.

FIGS. 4A-4C are perspective views showing example handle assemblies;

FIG. 5 is a perspective view showing an example rod hook of FIGS. 4A-4C;

FIGS. 6A-6G are perspective views showing example medical devices for reducing a rod into the head of a screw.

DETAILED DESCRIPTION

Implementations of the present disclosure now will be described more fully hereinafter. Indeed, these implementations can be embodied in many different forms and should not be construed as limited to the implementations set forth herein; rather, these implementations are provided so that this disclosure will satisfy applicable legal requirements. As used in the specification, and in the appended claims, the singular forms "a," "an," and "the," include plural referents unless the context clearly indicates otherwise. The term "comprising" and variations thereof as used herein is used synonymously with the term "including" and variations thereof and are open, non-limiting terms.

In performing a wide range of back surgeries, surgeons are often required to make use of pedicle screws and rods. These screws and rods are components of rigid stabilization systems, which tend to be intrusive to surrounding tissue and vasculature systems. When working with these rigid stabilization systems, surgeons often use instruments to insert the spinal rod into position in the receiving channel of a screw. Surgeons, however, have often encountered considerable difficulty in maneuvering the spinal rod into position in the receiving channel. The present disclosure provides devices and methods for urging spinal rods into the rod receiving channel formed in the spinal implants, which includes the capability to move the spinal rod in more than one direction. The surgeon is also able to use these disclosed devices and methods with only one hand.

Figure 1:
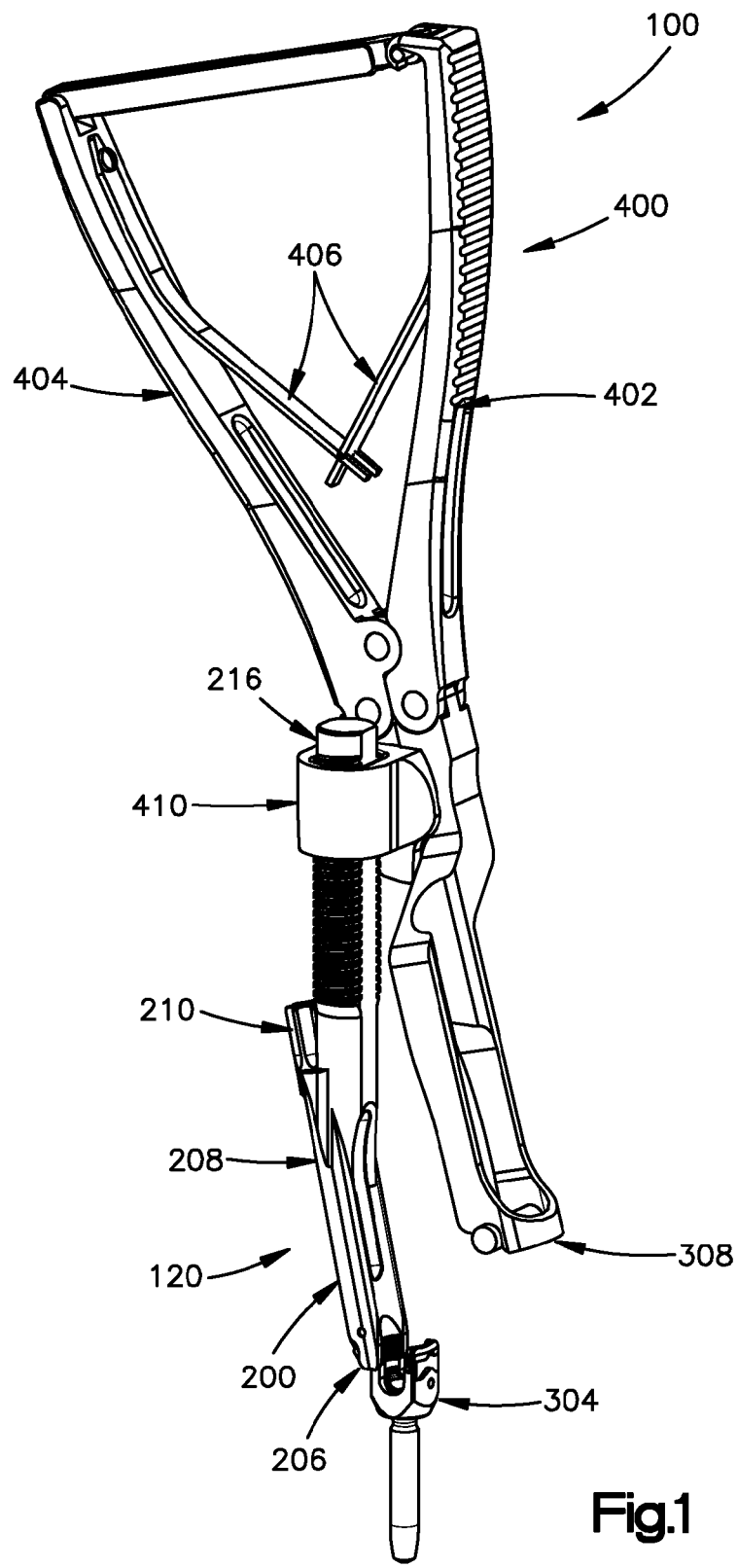
FIG. 1 is a perspective view showing an example medical device for reducing a rod into the head of a screw.

FIG. 1 shows an example medical device 100 for reducing a rod into the head of a screw or other bone attachment device. The example medical device 100 may include an implant holder 120, a handle assembly 400, a rod hook 408, and a guide 410. As shown in FIG. 1, the implant holder 120 includes a holding sleeve 200 with a securing foot 206 pivotally attached to a distal end of the holding sleeve 200. The holding sleeve 200 further includes a threaded opening 208 at a proximal end. The threaded opening 208 is adapted to receive a stem 210 that drives the securing foot 206 between a first position and a second position. The implant holder 120 also includes a threaded part 216 extending at a predetermined angle from the proximal end 202 of the holding sleeve 200. The threaded part 216 is adapted to engage a complementary threaded portion of a reduction knob (not shown in FIG. 1).

The securing foot 206 may be adapted to engage the head of a screw 304. In order for the securing foot 206 to fully engage the head of a screw 304, the implant holder is fully unthreaded so that the securing foot 206 is in the first or "open" position. The implant holder 120 may then be engaged on the side of the screw head 304 opposite the rod 500. Once the implant holder 120 is fully seated on the screw head 304, the stem 210 may be tightened by one's fingers or an appropriate driver. In order to ensure that the implant holder is securely fit atop of the screw head, the medical professional or other appropriate personnel may lightly pull up on the implant holder 120.

The handle assembly 400 includes two pivotally attached arms 402 and 404. A rod hook is 408 is connected to arm 402. The guide 410 is attached to arm 404. The guide 410 is adapted to slidably engage the threaded part 216, such that the rod hook 408 is moveable in a first direction. Movement in a first direction occurs by threaded interaction of the reduction knob with the threaded part 216. Further, pivotal motion of the arms 402 and 404 causes the rod hook 408 to be moveable in a second direction different than the first direction. A more detailed discussion of the movement of the rod caused by the device 100 is described below.

The handle assembly 400, including the guide 410 and rod hook 408, may be placed over the implant holder so that the rod hook 408 is positioned on the same side as the rod 600. The handle assembly 400 may be engaged with the implant holder 120, and the medical professional or other appropriate personnel squeezes arms 402 and 404 of the handle assembly until the rod hook 408 meets the top of the rod 500. Once the rod hook 408 meets the top of the rod 500, the reduction knob 214 (not shown) may then be threaded onto the proximal end of the implant holder 120.

The reduction knob 214 (not shown) may then be further advanced clockwise to achieve advancement of the rod hook 408 in the first direction. The arms 402 and 404 of the handle assembly may be squeezed to advance the rod hook 408 in a second direction. Advancement in the first and/or second direction may continue until the rod 500 engages the bottom of the rod slot in the head of the screw 304. Once the rod 500 has engaged the head of the screw 304 and is positioned correctly, a locking cap (not shown) may be introduced and tightened. The implant holder 120, handle assembly 400, rod hook 408, and guide 410 may then be removed by loosening the stem 210 on the implant holder to disengage the securing foot 206 from the head of the screw 304.

The above-described components of the medical device 100 will be described in further detail below. The example medical device 100 may provide reduction of a rod into the head of a screw when the rod is out of alignment in up to two different planes during spinal surgery. This medical device 100 may be used in the posterior thoracic and lumbar spine region for degenerative and deformity correction.

Figure 2C:
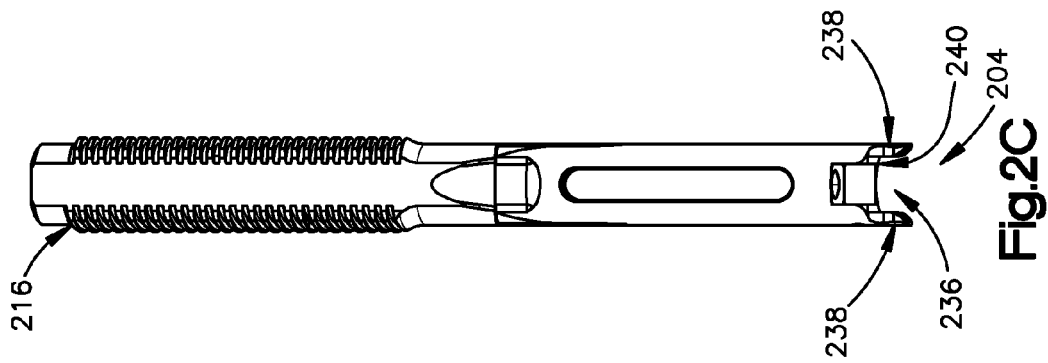
FIGS. 2B-2C are perspective views showing example holding sleeves.
Figure 2B:
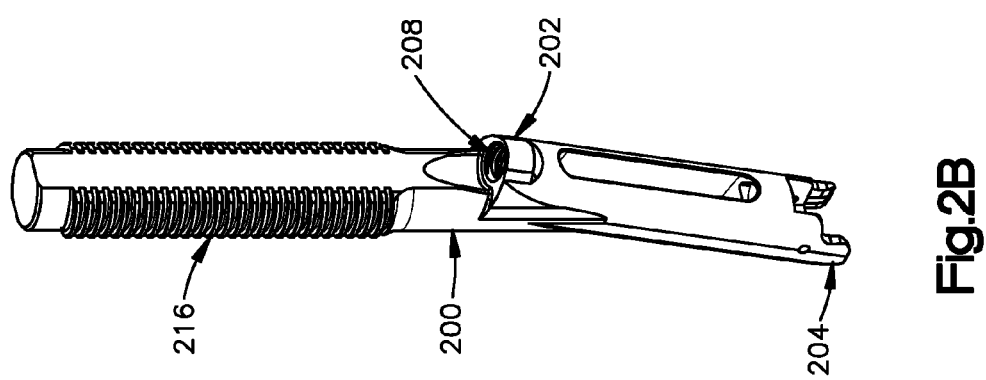
Figure 2A:
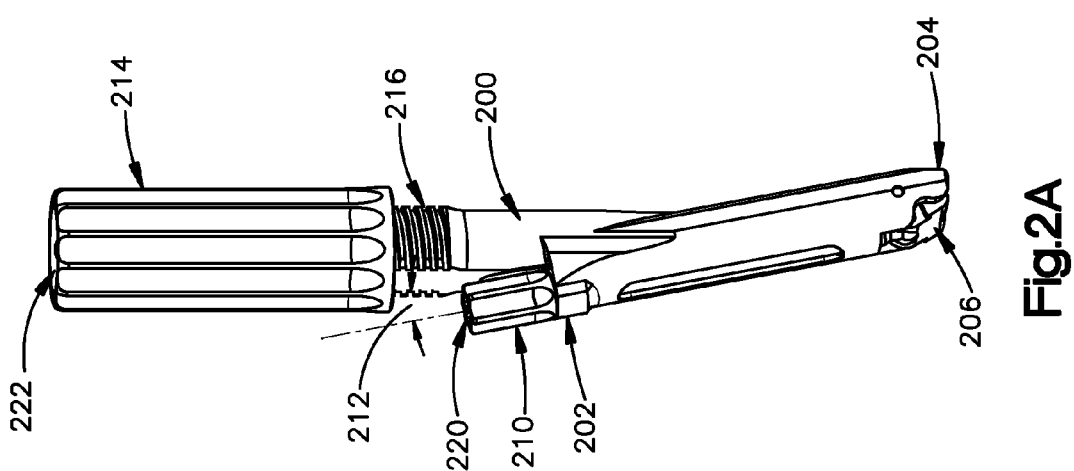
FIG. 2A is a perspective view showing an example implant holder.

Referring now to FIG. 2A, an example implant holder 120 is shown. The implant holder 120 includes a holding sleeve 200 having a proximal end 202 and a distal end 204. Example holding sleeves 200 are shown in FIGS. 2B and 2C. During spinal surgery, the holding sleeve 200 and securing foot 206 may be attached to a screw. Thus, the securing foot 206 provides for a secure fit, as well as a fit that does not hinder a medical professional's access to all the desired features used on the screw. For example, once a rod is reduced into the head of the screw, the medical professional must be able to introduce some locking mechanism, including but not limited to a locking screw, to lock the rod and screw together. Because the holding sleeve 200 and securing foot 206 are secured to only one side of the screw, the holding sleeve 200 provides access to the screw for introduction of a locking mechanism, once the rod is reduced into the head of the screw.

Referring to FIG. 2C, an example holding sleeve 200 is shown with the distal end 204 of the holding sleeve 200 as optionally defined on three sides. One side of the three sides may have a recessed portion 236. The two of the three unrecessed sides 238 may include concave areas for engaging a screw.

Figure 2D:
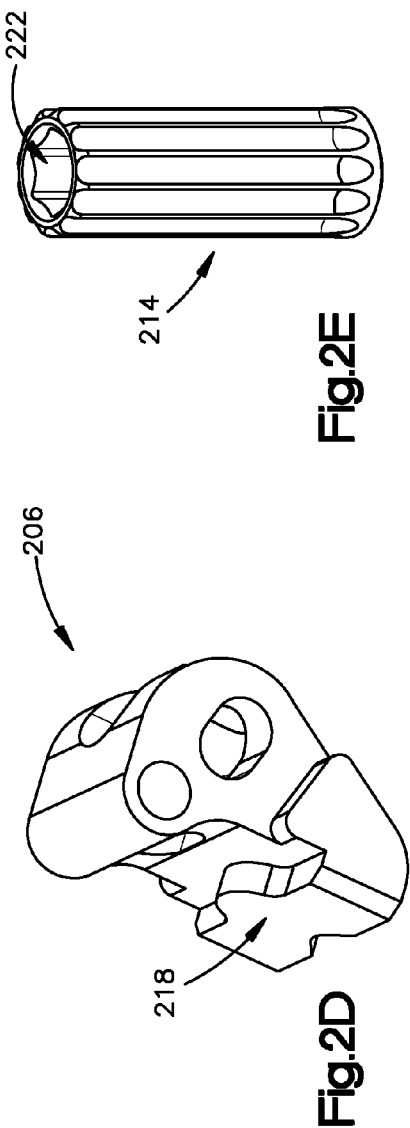
FIG. 2D is a perspective view showing an example securing foot.

A securing foot 206 is pivotally attached to the distal end 204 of the holding sleeve 200. An example securing foot 206 is shown in FIG. 2D. In order to facilitate engagement of the distal end 204 of the holding sleeve 200 with a screw head, the portion of the securing foot 206 engaging the screw may have a known geometry 218. This known geometry 218 of the securing foot 206 may be complementary to the known geometry of the screw to provide a secure fit between the securing foot 206 and the screw, as well as maximizes the contact area between the securing foot 206 and the screw. This known geometry 218 may vary to accommodate various screw designs, architecture, and/or other screw embodiments.

Figure 2E:
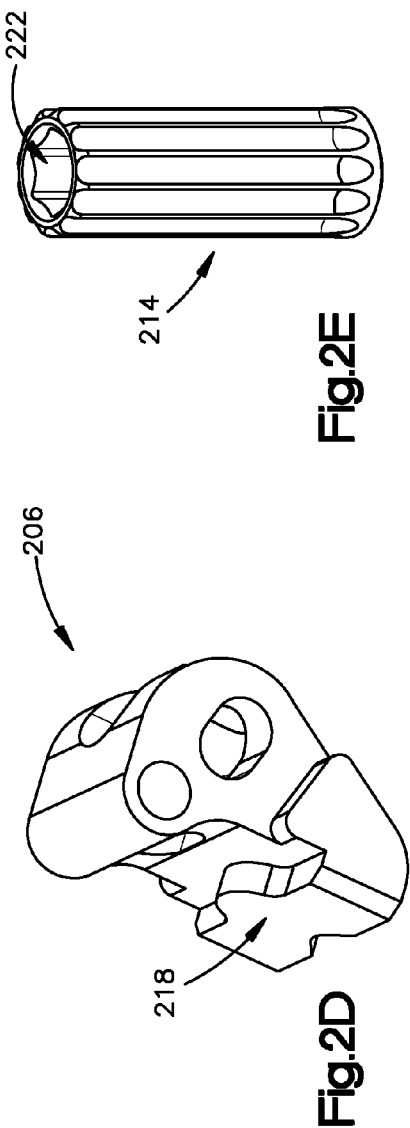
FIG. 2E is a schematic showing an example stem.

The holding sleeve 200 further includes a threaded opening 208 at the proximal end 202 of the holding sleeve 200. The threaded opening 208 is adapted to receive a stem 210 that drives the securing foot 206 between a first position and a second position. An example stem 210 is shown in FIG. 2E. The stem 210 may include a proximal end 226 and a distal end 224. The distal end 224 of the stem 210 may optionally include a spherical shape 228 and a ridge area 230. The shape on the distal end 224 of the stem 210 provides for ease of use when a medical professional rotates the stem to engage the securing foot 206 with the head of a screw. Further, the shape on the distal end 224 of the stem 210 provides a uniform shape that does not change the position and/or shape of stem 210 as stem 210 advances.

The stem 210 may optionally provide a securing cap 232 on the proximal end 226 of the stem 210. The superior portion of the securing cap 232 may include a recessed portion 220. The recessed portion 220 may be adapted to a known geometric shape for insertion of a tightening instrument therein. For example, a T25 driver 502 (as shown in FIGS. 6E-6F) may be used as a tightening instrument. Other appropriate or relevant tightening instruments may be used. Further, the recessed portion 220 of the stem 210 may be adapted to any known geometric shape for use with any complementary tightening instrument. A portion of the stem 210 proximate to the securing cap 232 may define a threaded region 234 for a predetermined distance, as shown in FIG. 2E. For example, the predetermined distance of the threaded region 234 is less than the length of the stem 210. This predetermined distance ensures that the male threads exit the female threads in such a way that prevents the user from over-loosening the stem and damaging the instrument. Similarly, the length 235 between the bottom of the securing cap 232 and the distal end 224 is predefined to act as a safety stop in order to prevent over-tightening of the stem 210 within the implant holder 120.

Figure 2F:
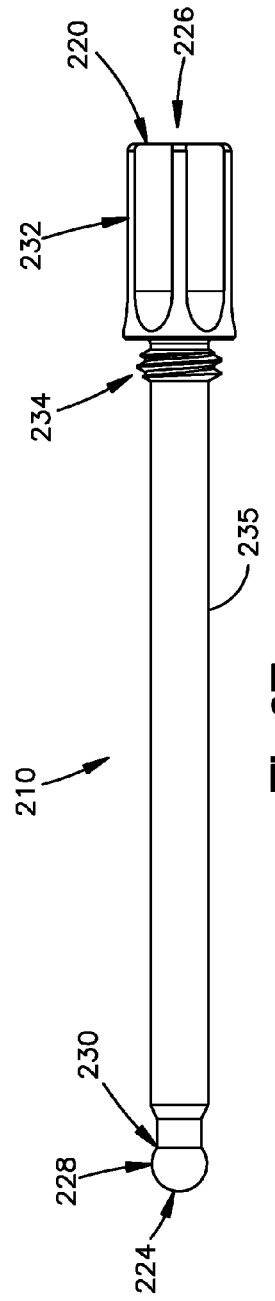
FIG. 2F is a perspective view showing an example reduction knob.

The implant holder 120 further includes a threaded part 216 extending at a predetermined angle 212 from the proximal end 202 of the holding sleeve 200. For example, the predetermined angle 212 optionally measures approximately 12°. Access during spinal surgery may be limited, so the angle measurement of 12° allows a medical professional adequate access. The threaded part 216 is adapted to engage a complementary threaded portion of a reduction knob 214. An example reduction knob 214 is shown in FIG. 2F.

Figure 2G:
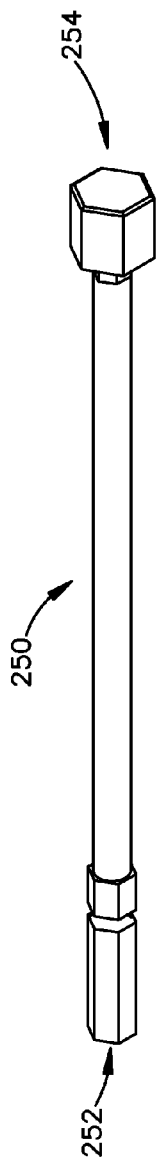
FIG. 2G is a schematic showing an example adapter rod.

Referring now to FIG. 2G, an example adapter rod 250 is shown. The adapter rod 250 may have a proximal end 252 and distal end 254. Both the proximal end 252 and distal end 254 of the adapter rod 250 may be defined in a known geometry. The distal end 254 may be engaged with the recessed portion 222 of the reduction knob 214. Any known geometry may be chosen for the distal end 254 or proximal end 252 of the adapter rod 250, or for the recessed portion 222 of the reduction knob 214. The adapter rod 250 may be rotated to advance the reduction knob 214 along the threaded part 216 in the first direction. Advancement of the reduction knob 214 along the threaded part 216 in the first direction causes the spinal rod to engage the screw. The threaded part 216 may be defined by a modified square thread measuring approximately 10°. A modified square thread may be used to allow medical professionals more efficiency and ease of use when engaging the complementary threads of the reduction knob 214 and threaded part 216.

The reduction knob 214 may optionally be comprised of polyether ether ketone (PEEK). This implant-grade PEEK material provides smooth threaded interaction along stainless steel and other metals. Implant-grade PEEK material also provides strength with minimized friction. The threaded portion 216 of the holding sleeve 200 may be coated in diamond-like carbon (DLC) coating or any other surface treatment to minimize friction or wear. DLC coating provides minimized friction on the threaded part 216, provides long-lasting threads, and protects the threaded part 216 (especially the parallel flat surfaces) as it slides through the guide 410 under extreme torque loads that result from maintaining the position of rod 500. These and the other components of the medical device may be comprised of any other metals or materials appropriate for surgical instruments and devices, including but not limited to stainless steel, titanium, CoCrMo, carbon fiber, and aluminum.

Figure 3C:
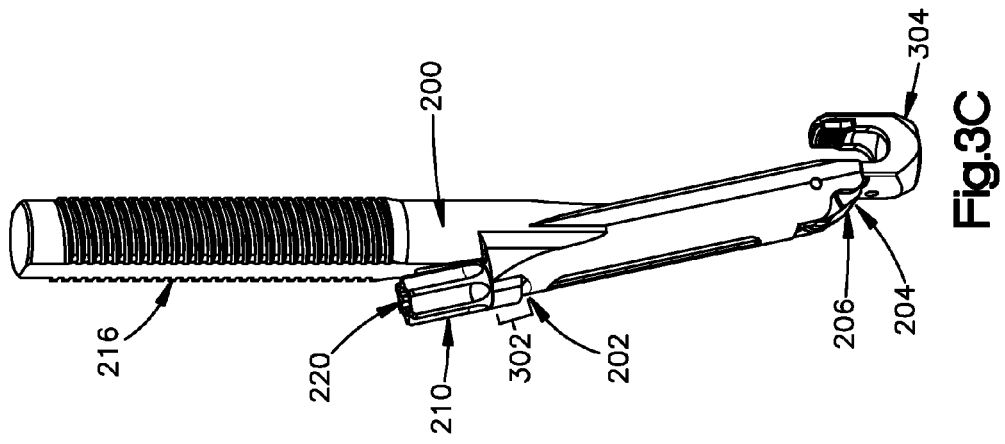
FIGS. 3A-3C are perspective views showing example implant holders for engaging a screw.
Figure 3B:
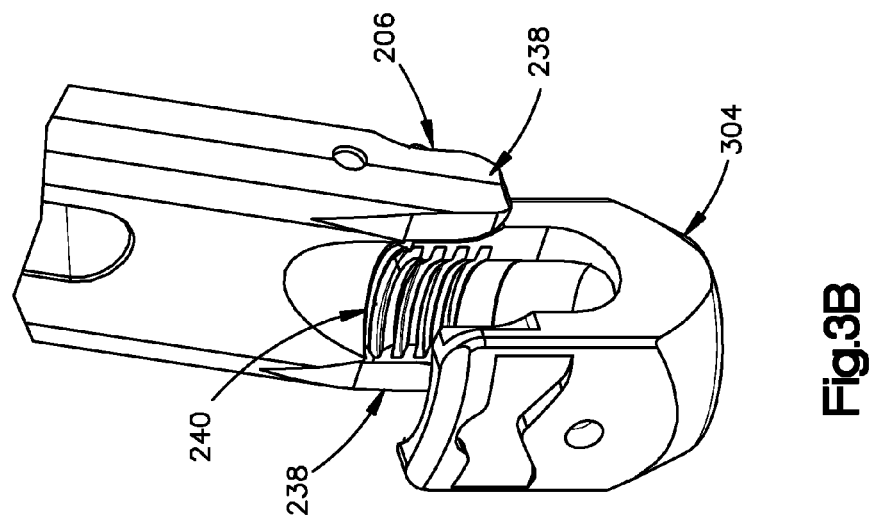
Figure 3A:
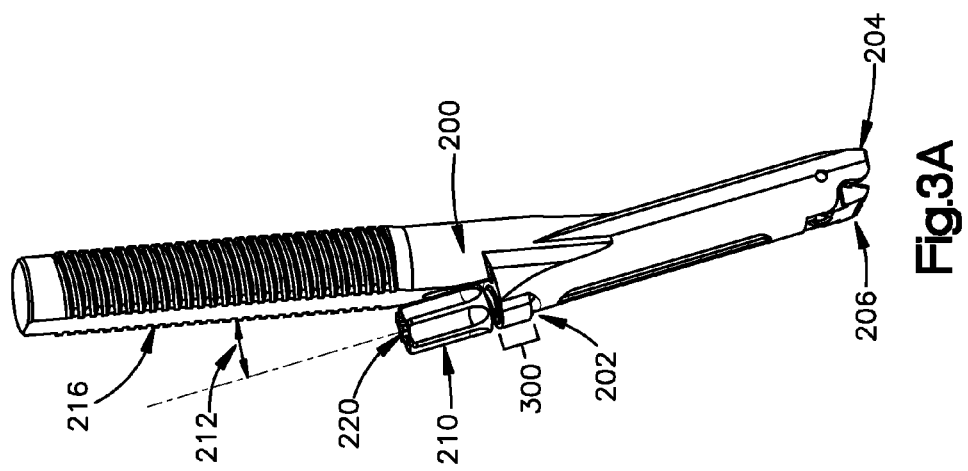

Referring now to FIGS. 3A-3C, there is illustrated an example engagement between the implant holder 129 and a screw 394 of the present disclosure. The securing foot 206 may have a first position 300 or a second position 302. For example, the first position 300 is optionally defined as wherein the threaded regions of the stem 210 and holding sleeve 200 are unthreaded. FIG. 3A shows an example implant holder 120 with the threaded regions of the stem 210 and holding sleeve 200 as unthreaded, and the securing foot 206 is optionally in a disengaged position.

FIG. 3B illustrates an example screw 304 engaged to a ridge portion 240. The distal end 204 of the holding sleeve 200 may include the ridge portion 240 for engaging a screw. During surgery, a medical professional may engage a screw with holding sleeve 200, and the ridge portion 240 may provide guidance to the medical professional to know when the holding sleeve 200 is seated atop the screw 304.

The securing foot 206 may also be defined as in a second position 302 wherein the stem is rotated therein the threaded opening of the holding sleeve 200. Referring to FIG. 3C, an example implant holder is shown with the threaded region 234 of the stem 210 and holding sleeve 200 as engaged. For example, rotation of the stem 210 into the threaded opening 208 of the holding sleeve 200 engages the securing foot 206 to the head of a screw 304.

Referring now to FIGS. 4A-4C, example handle assemblies 400 are shown. The handle assembly 400 includes two pivotally attached arms 402 and 404. A rod hook 408 is connected to arm 402. A guide 410 is attached to arm 404. The guide 410 is adapted to slidably engage a threaded part of the implant holder (FIG. 2A), such that the rod hook 408 is pivotally moveable in the second direction when the guide 410 engages the threaded part. For example, pivotal motion of the arms 402 and 404 causes the rod hook 408 to be moveable in the second direction, which is different than the first direction. As noted above, the first direction may be defined as substantially parallel along an axis defining the threaded part. The second direction may be defined as substantially parallel along an axis that may be approximated by an arc created by the movement of the rod hook 408. The guide 410 may be defined to cease travel of the rod hook 408 and the spinal rod in the second direction once the pivotally attached arms 402 and 404 are fully squeezed together. FIG. 5 illustrates the rod hook 408 in greater detail. As shown in FIG. 5, the distal end 418 of the rod hook 408 may include two concave portions 422 for engaging a spinal rod.

A lever 412 may also be provided with locking mechanisms along the length of lever 412. Complementary locking grooves may be provided on the proximal end of arm 404 to securely lock the handle assembly as the medical professional squeezes pivotally attached arms 402 and 404. Once at a position to stop, the medical professional can release the squeezing force, and the handle assembly may optionally lock into the latest position. This feature allows the medical professional to maintain a one-handed operation during the spinal surgery. Further, springs 406 may be provided between arms 402 and 404 to ensure a spring-loaded effect once the lever 412, if provided, is released from the locked position. When lever 412 is provided, the medical professional may engage and disengage lever 412 as necessary and as appropriate for the particular clinical situation. As shown in FIGS. 4A-4C, a guide 410 is optionally attached to the rod hook 408 with a pivot screw 414.

The arms 402 and 404 may be attached by screw 424, as shown in FIG. 4B. Arm 402 may be attached to rod hook 408 by screw 420. The guide 410 may be attached to the rod hook 408 by pivot screw 414, and the guide 410 may optionally be attached to arm 404 by screw 416. Screws 414, 416, 420, and 424 at the respective connection joints allow the rod hook 408 to move in the same direction as arms 402 and 404 when arms 402 and 404 are squeezed.

In accordance with another embodiment of the current disclosure the medical device may include an implant holder, a handle assembly, a rod hook, and a guide. The implant holder includes a holding sleeve 200, and the holding sleeve 200 has a proximal end 202 and a distal end 204. A securing foot 206 is pivotally attached to the distal end 204 of the holding sleeve 200. The holding sleeve 200 further includes a threaded opening 208 at the proximal end 202 of the holding sleeve 200. The threaded opening 208 is adapted to receive a stem 210 that drives the securing foot 206 between a first position and a second position. The implant holder further includes a threaded part 216 extending at a predetermined angle 212 from the proximal end 202 of the holding sleeve 200. The threaded part 216 is adapted to engage a complementary threaded portion of a reduction knob 214.

The handle assembly 400 includes two pivotally attached arms 402 and 404. A rod hook 208 is connected to arm 402. A guide 410 is attached to arm 404. The guide 410 is adapted to slidably engage the threaded part 216, such that the rod hook 408 is moveable in a first direction. Movement in a first direction occurs by threaded interaction of the reduction knob 214 with the threaded part 216. Movement in the first direction is defined as substantially parallel along an axis defining the threaded part. Further, pivotal motion of the arms 402 and 404 causes the rod hook 408 to be moveable in a second direction different than the first direction, as described above.

Figure 7:
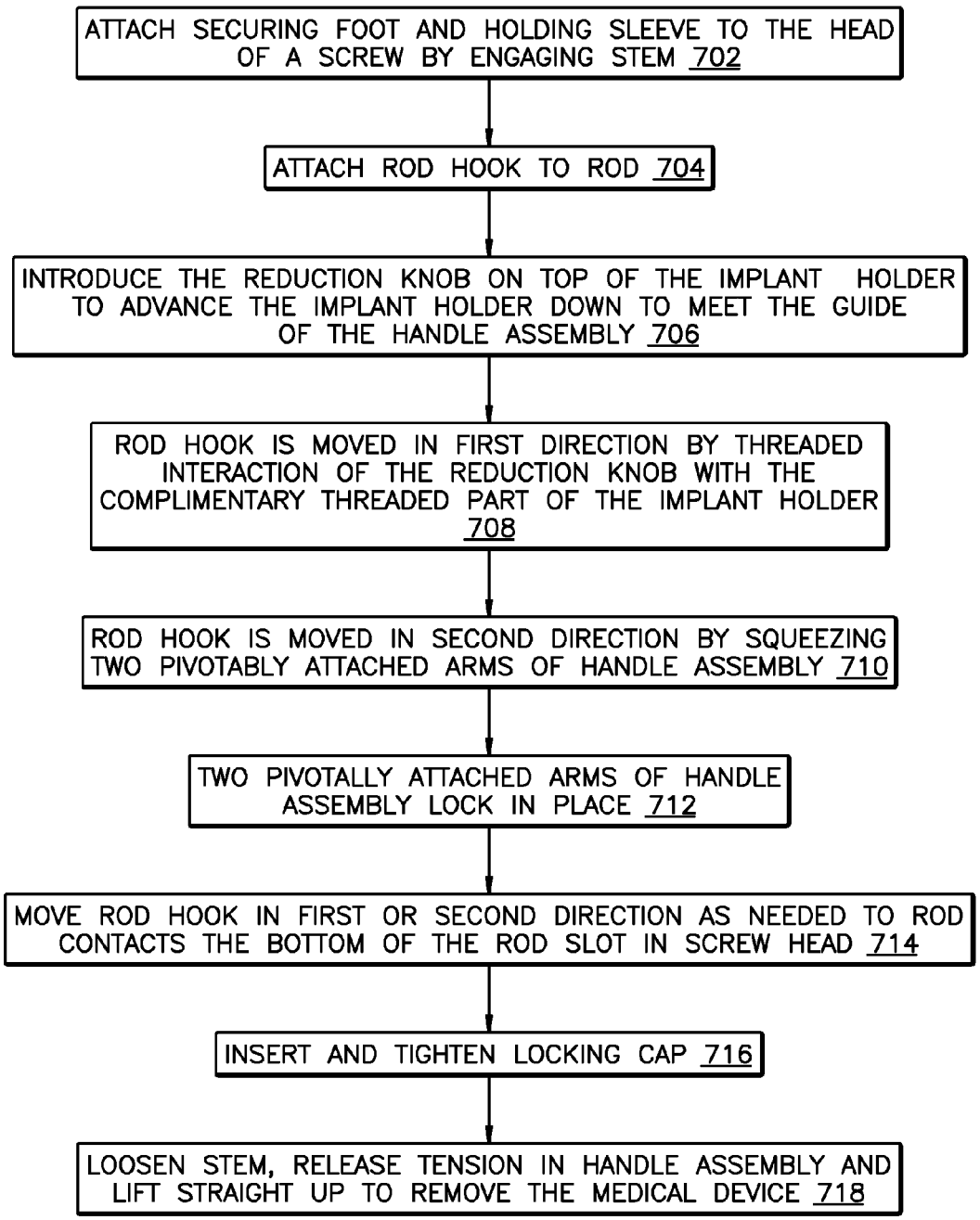
FIG. 7 illustrates an operational flow of reducing a rod into the head of a screw, as depicted in FIGS. 6A-6G.

In accordance with the present disclosure, there is also provided a method for reducing a rod into the head of a screw. Example methods are illustrated by FIGS. 6A-6G and an operational flow chart 700 in FIG. 7. The securing foot 206 and holding sleeve 200 may be attached a head of a screw 304 by the engaging stem (FIG. 6A; 702). The rod hook 408 may then be attached to the rod 500 (FIG. 6A; 704). The rod 500 may include any type of spinal rod. The method further includes advancing a securing foot 206 from a first position to a second position to attach the securing foot 206 and holding sleeve 200 to a screw 304 (FIG. 6A; 706). The rod hook 408 is moved in the first direction (FIGS. 6B and 6C; 708), and then moved in the second direction different than the first direction (FIGS. 6C and 6D; 710). For example, the first direction may be defined as substantially parallel along an axis defining the threaded part of the implant holder.

The rod hook 408 may be moved in the second direction by squeezing two pivotally attached arms 402 and 404. A lever 412 may also be provided with locking mechanisms along the length of lever 412 (FIG. 6E; 712). Complementary locking grooves may be provided on the proximal end of arm 404 to securely lock the handle assembly as the medical professional squeezes pivotally attached arms 402 and 404. Once at a position to stop, the medical professional can release the squeezing force, and the handle assembly may optionally lock into the latest position. This feature allows the medical professional to maintain a one-handed operation during spinal surgery.

A guide 410 may be adapted to slidably engage the threaded part 216 of the implant holder. The rod hook 408 is optionally moveable in the first direction by threaded interaction of the reduction knob 214 with the threaded part 216 (FIG. 6E; 714). Advancement in the first direction may reduce a rod 600 into a screw 304. A locking cap, or any other appropriate locking mechanism, may optionally be introduced to secure the rod 600 to the screw 304 (FIG. 6F; 716). Further, the securing foot 206 may be advanced from the second position to the first position to detach the securing foot 206 and holding sleeve 200 from the screw 304 (FIG. 6G; 718). In this method, advancement in the first direction may occur prior to advancement in the second direction. Alternatively, advancement in the second direction may occur prior to advancement in the first direction. Still further, the movement in the first and second direction may be iterative. A medical professional may adjust advancements in the various directions based on his expertise and relevant clinical settings.

In the above, the device 100 has been described as being secured to the screw 304 by performing a sequence of steps to attach and secure the securing foot 206 to the head of the screw 304. It is noted that the removal of the device 100 from screw 304 may be performed in a different reverse order than the order by which the device 100 was secured to the screw 304. As such, the user is enabled to can remove the device from the surgical site much more quickly during use.

Many modifications and other embodiments of the disclosure set forth herein will come to mind to one skilled in the art to which this disclosure pertains having the benefit of the teachings presented in the foregoing description. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A medical device adapted to be secured to a screw, comprising:
    an implant holder that includes a holding sleeve and a securing foot pivotally attached to a distal end of the holding sleeve, the holding sleeve defining a threaded opening at a proximal end thereof that receives a stem that drives the securing foot between a first position and a second position, the implant holder including a threaded part extending at an angle relative to the proximal end of the sleeve,
    the stem having a securing cap extending from a proximal end thereof such that a distance between the securing cap and a distal end of the stem is predetermined to prevent over-tightening or over-loosening of the stem, a portion of the stem proximate to the securing cap defining a threaded region extending over less than a length of the stem,
    wherein a portion of the securing foot has a known geometry complementary to a known geometry of the screw, and
    wherein the securing foot is sized and configured to be engaged to the screw when in the second position and disengaged from the screw when in the first position.

2. The medical device of claim 1, wherein the securing foot is in the first position when the threaded region of the stem and the threaded opening of the holding sleeve are uncoupled.

3. The medical device of claim 1, wherein the securing foot is in the second position when the stem is rotated about the threaded opening of the holding sleeve.

4. The medical device of claim 1, wherein the securing foot is sized and configured to engage only one side of a head of the screw.

5. A medical device for reducing a rod into a head of a screw, comprising:
    an implant holder that includes a holding sleeve, a securing foot pivotally attached to a distal end of the holding sleeve, the holding sleeve defining a threaded opening at a proximal end thereof that receives a stem that drives the securing foot between a first position and a second position, the implant holder including a threaded part extending at a predetermined angle from the proximal end of the holding sleeve that is adapted to engage a complementary threaded region of a reduction knob; and
    a handle assembly comprising two pivotally attached arms, a rod hook connected to one of the arms and a guide attached to the other of the arms; and
    wherein the guide is adapted to slidably engage the threaded part such that the rod hook is moveable in a first direction by threaded interaction of the reduction knob with the threaded part, and wherein pivotal motion of the arms causes the rod hook to be moveable in a second direction different than the first direction.

6. The medical device of claim 5, wherein a proximal end of the stem includes a securing cap.

7. The medical device of claim 6, wherein a portion of the stem proximate to the securing cap defines a threaded region.

8. The medical device of claim 5, wherein rotation of the stem into the threaded opening of the holding sleeve engages the securing foot to the screw head.

9. The medical device of claim 8, wherein a portion of the securing foot engaging the screw has a known geometry and is complementary to a known geometry of the screw.

10. The medical device of claim 5, wherein the distal end of the holding sleeve is defined having three sides, and wherein one side of the three sides has an opening defined therein.

11. The medical device of claim 5, wherein the predetermined angle of the threaded part of the implant holder is approximately 12°.

12. The medical device of claim 5, wherein the first direction is defined as substantially parallel along an axis defining the threaded part.

13. The medical device of claim 5, wherein the second direction is defined as being substantially parallel to an axis approximated by an arc created by the movement of the rod hook.

14. A medical device for reducing a rod into a head of a screw, comprising:
- an implant holder that includes a holding sleeve having a proximal end and a distal end, a securing foot pivotally attached to the distal end of the holding sleeve, the holding sleeve defining a threaded opening that receives a stem that drives the securing foot, the implant holder including a threaded part extending from the proximal end of the holding sleeve that is adapted to engage a complementary threaded region of a reduction knob; and
- a handle assembly comprising two pivotally attached arms, a rod hook connected to one of the arms and a guide attached to the other of the arms; and
- wherein the guide is adapted to slidably engage the threaded part such that the rod hook is moveable by threaded interaction of the reduction knob with the threaded part in a first direction defined as substantially parallel along an axis defining the threaded part, and wherein pivotal motion of the arms causes the rod hook to be moveable in a second direction defined as substantially parallel along an axis defining an arc that intersects the axis defining the threaded part.

15. The medical device of claim 14, wherein rotation of the stem into the threaded opening of the holding sleeve engages the securing foot to the screw head.

16. The medical device of claim 14, wherein a portion of the securing foot that engages the screw has a known geometry and is complementary to a known geometry of the screw.

17. The medical device of claim 14, wherein the guide is attached to the rod hook with a pivot screw.

* * * * *